(12) United States Patent
Parry et al.

(10) Patent No.: US 9,930,888 B2
(45) Date of Patent: Apr. 3, 2018

(54) COMPOSITION

(71) Applicant: Conopco, Inc., Englewood Cliffs, NJ (US)

(72) Inventors: Neil James Parry, Bunbury (GB); Joanne Clare O'Keeffe, Wirral (GB); Christopher Francis Smith, Mansfield (GB)

(73) Assignee: Conopco, Inc., Englewood Cliffs, NJ (US)

( * ) Notice: Subject to any disclaimer, the term of this patent is extended or adjusted under 35 U.S.C. 154(b) by 63 days.

(21) Appl. No.: 14/762,927

(22) PCT Filed: Jan. 29, 2014

(86) PCT No.: PCT/EP2014/051731
§ 371 (c)(1),
(2) Date: Jul. 23, 2015

(87) PCT Pub. No.: WO2014/118240
PCT Pub. Date: Aug. 7, 2014

(65) Prior Publication Data
US 2015/0351393 A1 Dec. 10, 2015

(30) Foreign Application Priority Data
Feb. 1, 2013 (EP) .................................. 13153600

(51) Int. Cl.
| | | |
|---|---|---|
| *A01N 43/36* | (2006.01) | |
| *A61K 8/49* | (2006.01) | |
| *A61K 8/34* | (2006.01) | |
| *A61Q 17/00* | (2006.01) | |
| *A61Q 19/10* | (2006.01) | |
| *A61Q 5/02* | (2006.01) | |
| *A61Q 5/12* | (2006.01) | |
| *A61Q 15/00* | (2006.01) | |
| *A01N 25/00* | (2006.01) | |
| *A61K 8/92* | (2006.01) | |
| *A61Q 11/00* | (2006.01) | |
| *A61K 8/69* | (2006.01) | |

(52) U.S. Cl.
CPC ............ *A01N 43/36* (2013.01); *A01N 25/00* (2013.01); *A61K 8/345* (2013.01); *A61K 8/4913* (2013.01); *A61K 8/69* (2013.01); *A61K 8/922* (2013.01); *A61Q 5/02* (2013.01); *A61Q 5/12* (2013.01); *A61Q 11/00* (2013.01); *A61Q 15/00* (2013.01); *A61Q 17/005* (2013.01); *A61Q 19/10* (2013.01); *A61K 2800/591* (2013.01)

(58) Field of Classification Search
CPC ........ A01N 43/36; A01N 25/00; A61K 8/922; A61K 8/345; A61K 8/4913; A61K 8/69; A61Q 5/02; A61Q 5/12; A61Q 11/00; A61Q 15/00; A61Q 17/005; A61Q 19/10
See application file for complete search history.

(56) References Cited

U.S. PATENT DOCUMENTS

| | | |
|---|---|---|
| 5,266,590 A | 11/1993 | Narayanan |
| 5,369,118 A | 11/1994 | Reizlein et al. |
| 2008/0095863 A1 | 4/2008 | Kabra |
| 2013/0237613 A1 | 9/2013 | Kim |

FOREIGN PATENT DOCUMENTS

| | | |
|---|---|---|
| CN | 1688543 | 10/2005 |
| DE | 3910921 | 5/1990 |
| EP | 2404502 | 1/2012 |
| KR | 20100068265 | 6/2010 |
| WO | WO9213454 | 8/1992 |
| WO | WO9827811 | 7/1998 |
| WO | WO9919256 | 4/1999 |
| WO | WO2004016588 | 2/2004 |
| WO | WO2007085042 | 8/2007 |
| WO | WO2008052031 | 5/2008 |
| WO | WO 2010/069742 | * 6/2010 |

OTHER PUBLICATIONS

Andersen et al., New Unstable Variants of Green Fluorescent Protein for Studies of Transient Gene Expression in Bacteria, Applied and Envrionmental Microbiology,, 1998, p. 2240-2246, 64 No. 6, US.
Christensen, Simpson, Younger, Baddour, Barrett, Melton, Beachey, Adherence of Coagulase-Negative Staphylococci to Plastic Tissue Culture Plates, Journal of Clinical Microbiology 1985 vol. 22 No. 6 p. 996-1006, 1985, pp. 996-1006, 22 No. 6, US.
Surette et al., Quorum sensing in *Escherichia coli*, Slamonella typhimurium, and Vibrio harveyi: A new family of genes responsible for autoinducer production, Proc. Natl. Acad. Sci USA 1999, 1999, pp. 1639-1644, 96.
Surette MG BL Bassler, Quorum sensin in *Escherichia coli* and *Salmonella typhimurium*, Proc Natl Acad Sci USA, 1998, pp. 7046-7050, 95, US.
Mar. 4, 2014, Search Report in PCTEP2014051731 (NPL 1, pp. 1-5).
Mar. 4, 2014, Written Opinion in PCTEP2014051731 (NPL 1, pp. 6-10).
Search Report in EP13153600, dated Mar 18, 2013 (NPL 1, pp. 11-13).
Written Opinion in EP13153600, dated Mar 18, 2013 (NPL 1, pp. 14-16).
Rosen et al., "Surfactants and Interfacial Phenomena"; pp. 212-215, 2012.

* cited by examiner

*Primary Examiner* — Johann R Richter
*Assistant Examiner* — Genevieve S Alley
(74) *Attorney, Agent, or Firm* — Greenberg Traurig, LLP

(57) ABSTRACT

Antimicrobial composition comprising a lactam and a hydrotrope. Antimicrobial additive composition containing a lactam and a hydrotrope.

12 Claims, 1 Drawing Sheet

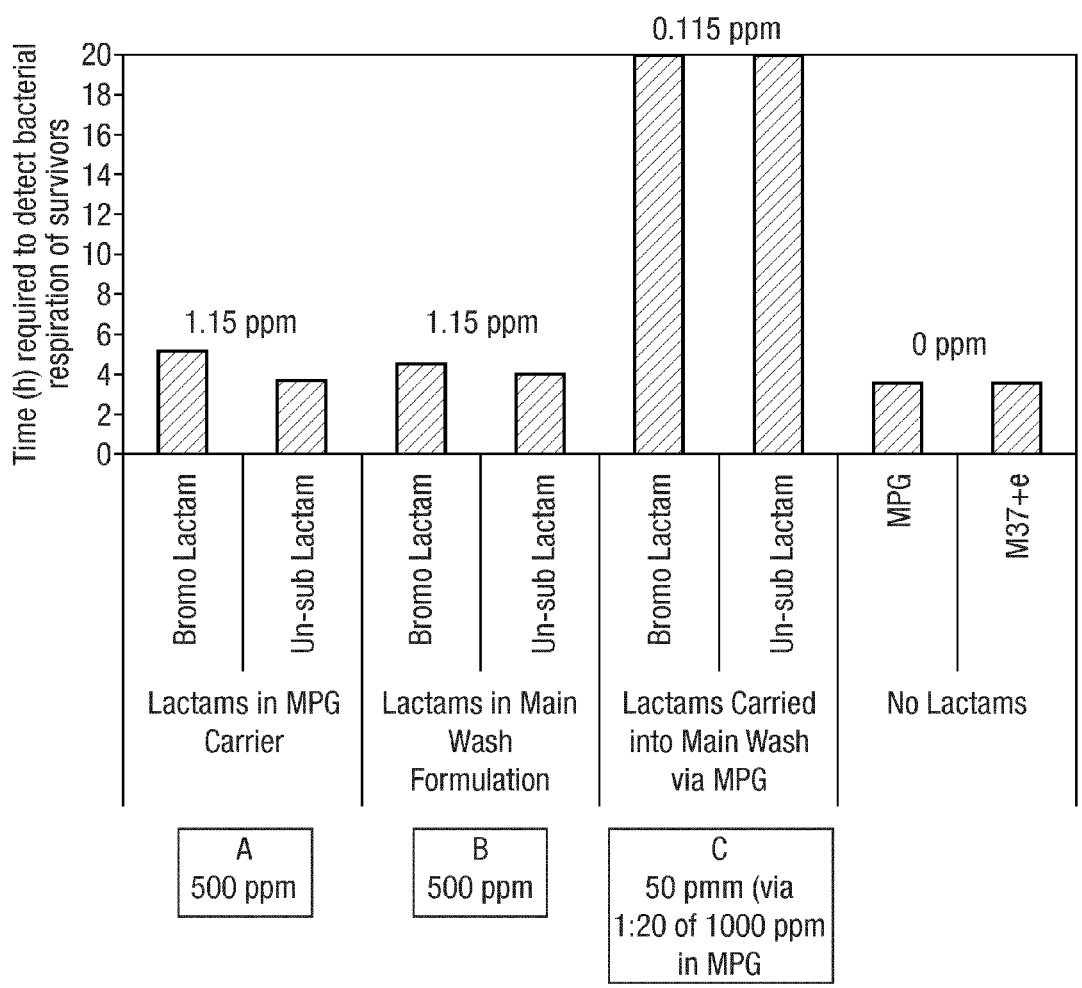

COMPOSITION

The present invention relates to an improved antimicrobial composition comprising a lactam.

WO 2007/085042 and WO 2004/016588 disclose lactams for antimicrobial benefit.

Despite the prior art there remains a need for improved antimicrobial compositions.

Accordingly, and in a first aspect of the present invention there is provided an antimicrobial composition comprising a lactam and a hydrotrope preferably wherein the lactam is of formula (I) or (II):

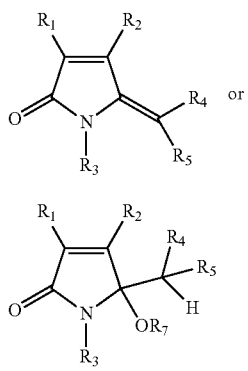

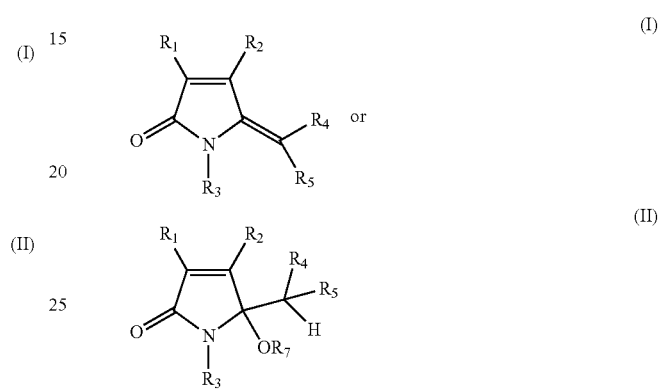

In a second aspect, there is provided an antimicrobial additive composition containing a lactam and a hydrotrope.

Preferably the anti-microbial composition and additive composition contains 0.000001 to 50% wt. lactam, more preferably 0.001 to 50% wt. even more preferably 0.01 to 5% wt, most preferably 0.01-2%.

In a third aspect of the invention there is provided an antimicrobial composition comprising an antimicrobial additive composition of the second aspect.

In a fourth aspect there is provided a method for making an antimicrobial composition comprising the steps:
(i) directly mixing a lactam with a hydrotrope to form an antimicrobial additive composition
(ii) mixing the antimicrobial additive composition of (i) with an aqueous carrier.

In a fifth aspect there is provided a method for making an antimicrobial additive composition comprising the step of directly mixing a hydrotrope with a lactam.

In a sixth aspect, the present invention provides the use of an antimicrobial composition according to the first and third aspect or an antimicrobial additive composition according to the second aspect for preventing or disrupting microbial growth.

Preferably the antimicrobial additive composition and the method of making said additive composition is substantially free of further components.

The term "substantially free" as used herein shall be understood to mean relatively little to no amount of any content. Preferably the antimicrobial contains less than 1 wt. % more preferably less than 0.1 wt. % of further components.

Preferably the aqueous carrier is suitable for use as a carrier for a home or personal care product. Preferred personal care products include shampoos, hair conditioners, deodorants, skin cleansing compositions and oral care products such as toothpastes and mouthwashes. Preferred home care products are for example a hard surface cleaner or laundry composition.

The antimicrobial additive composition according to the invention can be used as an antimicrobial raw material where it would be diluted in a further composition or the composition may be a consumer product the application of which is intended to provide antimicrobial effect to a substrate or even as a preservative when added to a consumer composition.

Preferably the lactam is of formula (I) or (II):

Preferably the lactam is of formula (I) or (II) wherein:
R1 and R2 are each independently selected from hydrogen, halogen, alkyl, cycloalkyl, alkoxy, oxoalkyl, alkenyl, heterocyclyl, heteroaryl, aryl and aralalkyl; and
R3 is selected from hydrogen, hydroxyl, alkyl, cycloalkyl, alkoxy, oxoalkyl, alkenyl, heterocyclyl, heteroaryl, cycloalkyl, aryl, aralalkyl and —C(O)CR6=CH2;
R4 and R5 are independently selected from hydrogen, aryl, heterocyclyl, heteroaryl, and arylalkyl; and
R6 is selected from hydrogen and methyl; and
R7 is selected from hydrogen and —C(O)CR6=CH2; and
Preferably, at least one of R4 and R5 is hydrogen; and
Preferably, at least one of R1 and R2 is selected from hetercyclyl, heteroaryl, aryl and arylalkyl; and
Preferably, R1 is hydrogen. Preferably, R3 is hydrogen. Preferably, R4 is hydrogen. Preferably, R5 is hydrogen. Preferably, R6 is hydrogen; and
Preferably, R2 is aryl or aralalkyl. More preferably, R2 comprises a halogen substituted phenyl group.

Preferably, the hydrotrope is selected from monopropylene glycol, dimethylsulphoxide, polyoxyethylene sorbitan fatty acid ester, polyoxyethylene derivatives of castor oil and ethanol.

Preferably, the hydroptrope is present at from 0.001 to 25% wt. of the composition.

Preferred lactams are:
5-methylene-4-(4'-bromophenyl)-dihydroprrol-2-one (Ref. 295)
5-methylene-4-(2'-fluorophenyl)-dihydropyrrol-2-one (Ref. 310)
5-methylene-4-phenyl-1H-pyrrol-2(5H)-one (Ref. unsubstituted)
methyl 2-(3-(4-fluorophenyl)-2-methylene-5-oxo-2,5-dihydro-1H-pyrrol-1-yl) (Ref. 309)
3-Bromo-4-hexyl-5-(bromomethylene)-2(5H)-furanone (Ref. 113)
4-(4-Trifluoromethyl)phenyl)-2(5H)-furanone (Ref. 265)

5-Hydroxy-5-methyl-4-(2'-fluorophenyl)-dihydropyrrol-2-one (Ref. 313)

5-(Thiophenyl-3-methylene)furan-(2H)-one (Ref. 350)

The most preferred lactams are:

5-methylene-4-(4'-bromophenyl)-dihydroprrol-2-one (Ref. 295)

5-methylene-4-(2'-fluorophenyl)-dihydropyrrol-2-one (Ref. 310)

5-methylene-4-phenyl-1H-pyrrol-2(5H)-one (Ref. unsubstituted)

methyl 2-(3-(4-fluorophenyl)-2-methylene-5-oxo-2,5-dihydro-1H-pyrrol-1-yl) (Ref. 309)

Preferably, the hydrotrope is selected from monopropylene glycol, dimethylsulphoxide, polyoxyethylene sorbitan fatty acid ester, polyoxyethylene derivatives of castor oil and ethanol.

Preferably, the polyoxyethylene sorbitan fatty ester is a monoester selected from monolaurate, monopalmitate, monostearate and monooleate.

Preferably, the polyoxyethylene sorbitan fatty ester comprises from 5 to 80 oxyethylene units, more preferably from 10 to 45 and most preferably 20. Examples include Polysorbates 20, 40, 60 and 80.

The most preferred polyoxyethylene sorbitan fatty ester is Polysorbate 20.

Preferably, the polyoxyethylene derivative of castor oil comprises from 10 to 50 oxyethylene units, more preferably from 30 to 45 and most preferably 40. Examples include PEG-20, 40 and 60 hydrogenated castor oil.

The most preferred polyoxyethylene derivative of castor oil is PEG-40 hydrogenated castor oil.

Preferably, the composition is a home care or personal care product.

Preferred personal care products include shampoos, hair conditioners, deodorants, skin cleansing compositions and oral care products such as toothpastes and mouthwashes. Preferred home care products include a hard surface cleaner or laundry composition.

Lactams

Suitable lactams are disclosed in WO 2007/085042 and WO 2004/016588 the contents of which with particular regard to the manufacture of lactams and from WO 2007/085042 the manufacture of acrylate polymers with certain lactams associated thereto, is incorporated by reference.

For example:

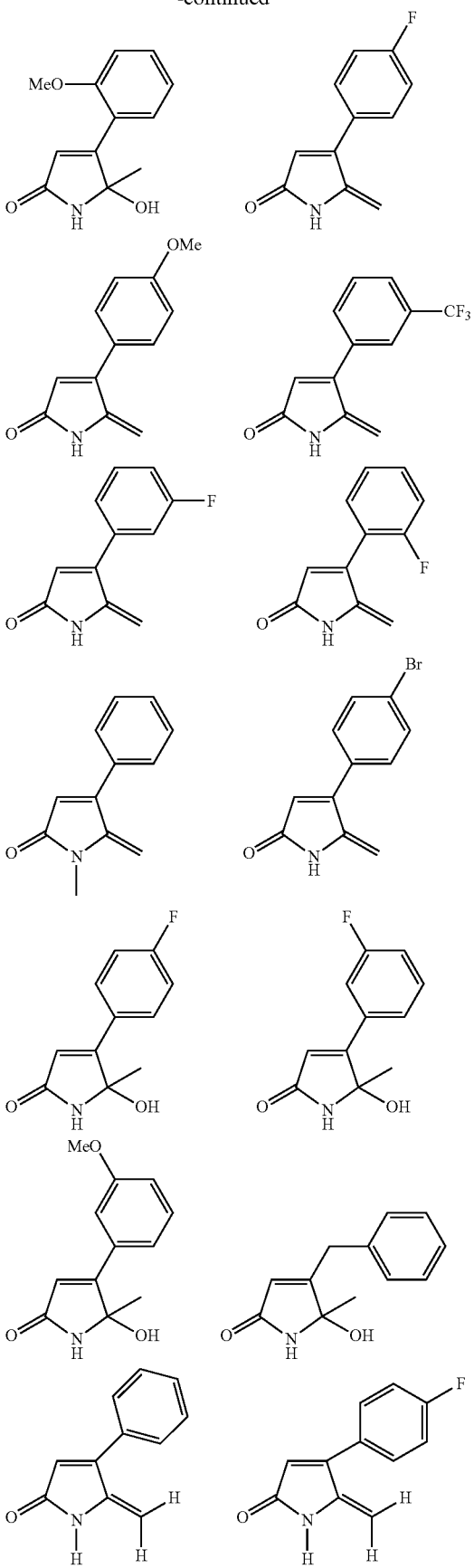

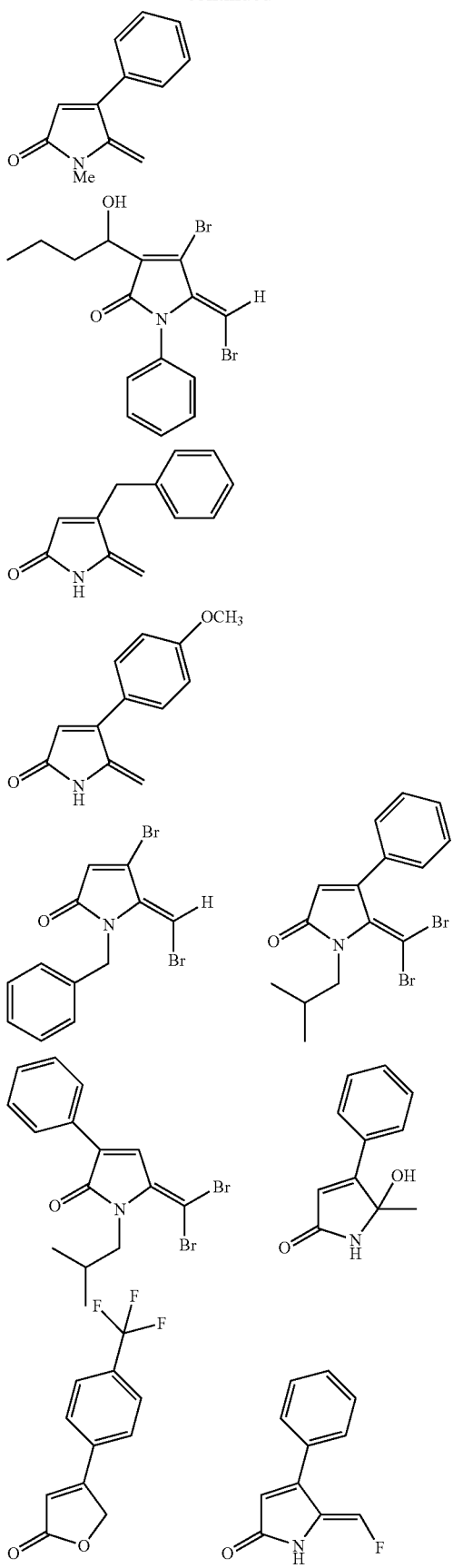
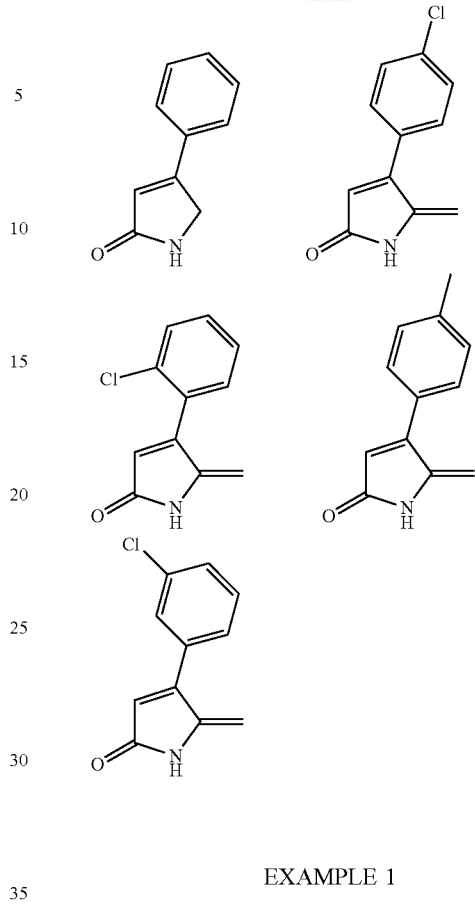

EXAMPLE 1

The following data illustrates the antimicrobial efficacy of a laundry composition (hereinafter 'base composition') comprising a lactam (Ref. 295 and Ref. Unsubstituted) and a hydroptrope (monopropylene glycol) but only where hydroptrope is mixed with lactam before adding to the remainder of the composition. The test samples were as follows:

A lactam and hydroptrope only

B lactam added directly to base formulation (which contains MPG)—no pre-mixing prior to addition C lactam pre-mixed with hydrotrope and then added to base formulation D hydrotrope only added to base formulation Base Formulation

| % activity | % required | Component | Amount in 100 g |
|---|---|---|---|
| 100 | 45.87 | Demin Water | 39.05 |
| 100 | 4.13 | Glycerol | 4.13 |
| 100 | 7.43 | Mono Propylene Glycol (with or without lactam according to BDC above) | 7.43 |
| 47 | 2.12 | NaOH | 4.51 |
| 100 | 2.10 | Triethanolamine (TEA) | 2.10 |
| 100 | 16.59 | Primary Alcohol Ethoxylate (7EO) | 16.59 |
| 68 | 0.10 | Optical Brightener | 0.15 |
| 50 | 0.81 | Citric Acid | 1.62 |
| 97.1 | 11.06 | LAS Acid | 11.39 |
| 100 | 3.10 | Fatty Acid | 3.10 |

-continued

| % activity | % required | Component | Amount in 100 g |
|---|---|---|---|
| 70 | 5.53 | SLES 3EO | 7.90 |
| 32 | 0.41 | Diethylenetriamine penta(methylene phosphonic acid) | 1.28 |
| 100 | 0.75 | Liquid Protease | 0.75 |
|  | 100.00 |  |  |

Test samples were diluted in sterile water to achieve a 11.5 ppm level of lactam. Dilute solution (80 μl) was added to a *S. epidermidis* suspension (20 μl) of bacteria at a concentration of 8 logs in a microplate. Growth media (100 μl tryptone soya broth) was added to each well of the microplate and incubated for 20 hours. Bacterial respiration was measured every 30 minutes and the results were:

A—lactam+hydrotrope only (respiration of surviving bacteria detected ~4-5 h)
B—lactam added directly to base formulation (which contains MPG)—no pre-mixing prior to addition (respiration of surviving bacteria detected 4-5 hrs)
C—lactam pre-mixed with hydrotrope and then added to base formulation (respiration of surviving bacteria not detected—20 hrs is max detection time)
D—hydrotrope added to base formulation (respiration of surviving bacteria detected 3-4 hrs).

The results are shown in FIG. 1.

EXAMPLE 2

The following illustrates the broad application of the invention within the realm of lactams The example below is from data obtained when pre-blending lactams with hydrotrope before adding to the .

remainder of the composition, and diluting to 11.5 ppm and 0.575 ppm in sterile water in order to assess efficacy against *S. epidermidis* suspension Dilute solution (80 μl) was added to a *S. epidermidis* suspension (20 μl) of bacteria at a concentration of 8 logs in a microplate. Growth media (100 μl tryptone soya broth) was added to each well of the microplate and incubated for 20 hours. Bacterial respiration was measured every 30 minutes. Data of the test samples were then compared to un-treated cell suspensions (sterile water added instead of test samples) and percent inhibition calculated.

| Test | Result (inhibition of bacterial respiration versus water control) |
|---|---|
| 5-methylene-4-(2'-fluorophenyl)-dihydropyrrol-2-one | 79.4% |
| 5-methylene-4-(4'-bromophenyl)-dihydroprrol-2-one | 82.5% |
| 5-methylene-4-phenyl-1H-pyrrol-2(5H)-one | 82.5% |

EXAMPLE 3

The aim of this example was to investigate methods of achieving solubility of 5-methylene-4-phenyl-1H-pyrrol-2(5H)-one (Ref. unsubstituted) into the following above described base formulation.

An Ultrasonic mixer was used to obtain determine solubility.

We used a Hielscher UP200S (200W) Sonic Tip on batches of 5-20 ml. We sonicated for up to 60 minutes.

| % lactam in solvent | Mixing method | Observations of solvent solution | Observations when added to base @ 5% |
|---|---|---|---|
| 3% in Polysorbate 20 | Magnetic stirring 1 hour | ~25% of lactam solubilised. Particles visible. | Clear solution with a large quantity of particles visible |
| 3% in PEG-40 Hydrogenated Castor Oil | Magnetic stirring 1 hour | ~25% of lactam solubilised. Particles visible. | Clear solution with a large quantity of particles visible |
| 3% in Isopentyldiol | Magnetic stirring 1 hour | No solubility observed. | — |
| 3% in MMB | Magnetic stirring 1 hour | No solubility observed. | — |
| 3% in Diglycerin | Magnetic stirring 1 hour | No solubility observed. | — |
| 3% in Diglycerin | Magnetic stirring 1 hour | No solubility observed. | — |
| 3% in Pentylene Glycol | Magnetic stirring 1 hour | No solubility observed. | — |
| 3% in Hexylene Glycol | Magnetic stirring 1 hour | No solubility observed. | — |
| 3% in Hexylene Glycol | Magnetic stirring 1 hour | No solubility observed. | — |
| 3% in PEG-60 Hydrogenated Castor Oil | Magnetic stirring 1 hour | ~10% of lactam solubilised. Particles visible. | Cloudy in solution |
| 3% in Polysorbate 60 | Magnetic stirring 1 hour, 50 C. | ~10% of lactam solubilised. Particles visible. | Cloudy and gel-like lumps in solution |

-continued

| % lactam in solvent | Mixing method | Observations of solvent solution | Observations when added to base @ 5% |
|---|---|---|---|
| 3% in Polysorbate 80 | Magnetic stirring 1 hour | ~10% of lactam solubilised. Particles visible. | Cloudy and gel-like lumps in solution |
| 3% in Dipropylene Glycol | Magnetic stirring 1 hour | ~5% of lactam solubilised (slight colour change observed showing this. Particles visible. | — |
| 3% in Sorbitan Oleate | Magnetic stirring 1 hour, 50 C. | ~5% of lactam solubilised (slight colour change observed showing this. Particles visible. | Cloudy when cooled or added to M30 |
| 3% in Sisterna SP30-C | Magnetic stirring 1 hour | ~5% of lactam solubilised (slight colour change observed showing this. Particles visible. | Cloudy solution with large number of particles visible. |
| 3% in Sisterna SP50-C | Magnetic stirring 1 hour | ~5% of lactam solubilised (slight colour change observed showing this. Particles visible. | Hazy solution with large number of particles visible. |
| 3% in Sisterna SP70-C | Magnetic stirring 1 hour | ~5% of lactam solubilised (slight colour change observed showing this. Particles visible. | Cloudy solution with large number of particles visible. |

The polysorbates and Pegylated castor oil were considered suitable enough to pursue further experimentation.

Further Evaluations with Each Candidate Solubiliser

We then tested the candidate solubilisers with 1% lactam, both with 72 hours high speed magnetic stirring (with held temperature of ~500 in the cases of solubilisers that solidify alone at room temperature) and also 20 minutes Sonication.

Preparation of the Lactam Solutions

In each case we incorporated the lactam powder into the solubilisers (at the levels indicated in the below table) using high speed stirring to avoid lumps from forming. Once the powder was added, the described mixing method (either continued high speed stirring or Ultrasonic mixing) commenced. In the cases of Sorbitan Oleate and Polysorbate-60, we applied initial heating to approx. 500 to ensure the solubilisers were fully liquid prior to commencing addition of the lactam. Both of these materials are non-flowing at room temperature. PEG-40 Hydrogenated Castor required initial heating to ~350 to ensure complete fluidity prior to commencing.

Incorporation of the Lactam Solutions into Base

The base sample provided had a 5% 'gap' purposely left out as space for the lactam solution to be added. We ensured the lactam solutions were fully uniform through constant mechanical agitation (to avoid the settling of any unsolubilised lactam material) and added them to base using slow speed stirring to incorporate them without generating aeration.

Stability Testing

We conducted stability testing on all test variants that looked positive (i.e. a reasonable proportion of lactam was solubilised). We prepared samples of the test variants in clear plastic jars and placed them at various temperature conditions:

Ambient temperature.
40 C.
50 C.
Refrigerator.
High light ('shop' window).

The aim was to observe any difference in colour, viscosity, solubility or general physical stability. The samples were evaluated every day and compared to the ambient temperature sample to note any changes. All samples were allowed to equilibrate to ambient temperature before being evaluated.

Isopentyldiol

| % lactam in solvent | Mixing method | Observations of solvent solution | Observations when added to M30 @ 5% |
|---|---|---|---|
| 1% in Isopentyldiol | Magnetic stirring 72 hours | No solubility observed at any stage. | — |
| 1% in Isopentyldiol | 20 minutes sonication. Temp reached 60-70 C. | ~5% of lactam solubilised (forced). Large number of particles visible. | — |

3-Methoxy-3-methyl-1-butanol

| % lactam in solvent | Mixing method | Observations of solvent solution | Observations when added to M30 @ 5% |
|---|---|---|---|
| 1% | Magnetic stirring 72 hours | No solubility observed at any stage. | — |
| 1% | 20 minutes sonication. Temp reached 60-70 C. | ~5% of lactam solubilised (forced). Large number of particles visible. | — |

Diglycerin

| % lactam in solvent | Mixing method | Observations of solvent solution | Observations when added to M30 @ 5% |
|---|---|---|---|
| 1% | Magnetic stirring 72 hours | No solubility observed at any stage. | — |
| 1% | 20 minutes sonication. Temp reached 60-70 C. | No solubility observed. | — |

Pentylene Glycol

| % lactam in solvent | Mixing method | Observations of solvent solution | Observations when added to M30 @ 5% |
|---|---|---|---|
| 1% | Magnetic stirring 72 hours | ~5% of lactam solubilised. Large number of particles visible. | — |
| 1% | 20 minutes sonication. Temp reached 60-70 C. | ~5% of lactam solubilised. Large number of particles visible. | — |

PEG-60 Hydrogenated Castor Oil

| % lactam in solvent | Mixing method | Observations of solvent solution | Observations when added to M30 @ 5% |
|---|---|---|---|
| 1% | Magnetic stirring 72 hours at 50 C. | ~25% of lactam solubilised. Particles visible. | Cloudy in solution. Particles visible. |
| 1% | 20 minutes sonication. Temp reached 60-70 C. | ~25% of lactam solubilised. Particles visible. | Cloudy in solution. Particles visible. |

Polysorbate 60

| % lactam in solvent | Mixing method | Observations of solvent solution | Observations when added to M30 @ 5% |
|---|---|---|---|
| 1% | Magnetic stirring 72 hours at 50 C. | ~25% of lactam solubilised. Particles visible. | Cloudy in solution. Particles visible. |
| 1% | 20 minutes sonication. Temp reached 60-70 C. | ~25% of lactam solubilised. Particles visible. | Cloudy in solution. Particles visible. |

Polysorbate 80

| % lactam in solvent | Mixing method | Observations of solvent solution | Observations when added to M30 @ 5% |
|---|---|---|---|
| 1% | Magnetic stirring 72 hours at 50 C. | ~25% of lactam solubilised. Particles visible. | Cloudy in solution. Particles visible. |
| 1% | 20 minutes sonication. Temp reached 60-70 C. | ~25% of lactam solubilised. Particles visible. | Cloudy in solution. Particles visible. |

Sisterna SP30-C

| % lactam in solvent | Mixing method | Observations of solvent solution | Observations when added to M30 @ 5% |
|---|---|---|---|
| 1% | Magnetic stirring 72 hours at 50 C. | ~25% of lactam solubilised. Particles visible. | Cloudy in solution. Particles visible. |
| 1% | 20 minutes sonication. Temp reached 60-70 C. | ~25% of lactam solubilised. Particles visible. | Cloudy in solution. Particles visible. |

Sisterna SP50-C

| % lactam in solvent | Mixing method | Observations of solvent solution | Observations when added to M30 @ 5% |
|---|---|---|---|
| 1% | Magnetic stirring 72 hours at 50 C. | ~25% of lactam solubilised. Particles visible. | Cloudy in solution. Particles visible. |
| 1% | 20 minutes sonication. Temp reached 60-70 C. | ~25% of lactam solubilised. Particles visible. | Cloudy in solution. Particles visible. |

Sisterna SP70-C

| % lactam in solvent | Mixing method | Observations of solvent solution | Observations when added to M30 @ 5% |
|---|---|---|---|
| 1% | Magnetic stirring 72 hours at 50 C. | ~25% of lactam solubilised. Particles visible. | Cloudy in solution. Particles visible. |
| 1% | 20 minutes sonication. Temp reached 60-70 C. | ~25% of lactam solubilised. Particles visible. | Cloudy in solution. Particles visible. |

Polysorbate 20

| % lactam in solvent | Mixing method | Observations of solvent solution | Observations when added to M30 @ 5% |
|---|---|---|---|
| 3% | Magnetic stirring 1 hour | ~25% of lactam solubilised. Particles visible. | Clear solution with a large quantity of particles visible |
| 4.2% | Magnetic stirring. 24 hours | ~25% of lactam solubilised, Particles visible. | Clear solution with a large quantity of particles visible |
| 4.2% | Magnetic stirring. 24 hours. | ~25% of lactam solubilised, Particles visible. Initially stirred for 2, 4 and 6 hours. No real changed observed during this time (all max. 25% solubilised). | Clear solution with a large quantity of particles visible |
| 4.2% | 20 minutes sonication. Temp reached 60-70 C. | ~50% of lactam solubilised. Particles visible | Clear solution with a large quantity of particles visible |
| 4.2% | 60 minutes sonication. Temp reached 90 C. | ~60-70% of lactam solubilised. Particles visible | Clear solution with a large quantity of particles visible |
| 2.1% | 20 minutes sonication. Temp reached 60-70 C. | ~90% of lactam solubilised. Dark colour formed | Clear solution. A very small number of remaining unsolubilised lactam particles visible |
| 2.1% | 60 minutes sonication. Temp reached 90-100 C. | 90% of lactam solubilised. Some small particles visible. | Clear solution with a minute number of particles visible. |
| 4.2% | Magnetic stirring. 48 hours. | ~25% of lactam solubilised, Particles visible. | Clear solution with a large quantity of particles visible |
| 2.1% | Magnetic stirring. 24 hours | ~50% of lactam solubilised, Particles visible. | Clear solution with a large quantity of particles visible |
| 2.1% | Magnetic stirring. 48 hours | ~75% of lactam solubilised, Particles visible. | Clear solution with a large quantity of particles visible |
| 2.1% | Magnetic stirring, heated to 50 C. 8 hours. | ~50% of lactam solubilised, Particles visible. | Clear solution with a large quantity of particles visible |
| 3% | 20 minutes sonication. Temp reached 60-70 C. | ~50% of lactam solubilised. Particles visible | Clear solution with a large quantity of particles visible |

| % lactam in solvent | Mixing method | Observations of solvent solution | Observations when added to base @ 5% |
|---|---|---|---|
| 3% | 60 minutes sonication. Temp reached 90 C. | ~60-70% of lactam solubilised. Particles visible | Clear solution with a large quantity of particles visible |
| 1% | Magnetic stirring. 24 hours | ~75% of lactam solubilised, Particles visible. | Clear solution with a few particles visible |
| 1% | Magnetic stirring. 72 hours | ~95% of lactam solubilised A few particles visible. After 48 hours it was approx. 80-85%. | Clear solution with a few particles visible |
| 2.1% | Magnetic stirring, heated to 50 C. 72 hours. | ~75% of lactam solubilised, Particles visible. | Clear solution with a large quantity of particles visible |
| 1.5% | Magnetic stirring. 48 hours | ~50% of lactam solubilised, Particles visible. | Clear solution with a large quantity of particles visible |
| 1.5 | Magnetic stirring, heated to 50 C. 72 hours. | ~75% of lactam solubilised, Particles visible. | Clear solution with a large quantity of particles visible |
| 1.5% | 20 minutes sonication. Temp reached 60-70 C. | ~75% of lactam solubilised. Some Particles visible | Clear solution with a number of particles visible |

| | | | |
|---|---|---|---|
| 1.5% | 60 minutes sonication. Temp reached 80-90 C. | ~95% of lactam solubilised. Particles visible. Dark brown colour. | Clear solution with a minute number of particles visible |
| 2.1% | 60 minutes sonication. Temp reached 80 C. | 90% of lactam solubilised. Some small particles visible. | Clear solution with a minute number of particles visible. |

PEG-40 Hydrogenated Castor Oil

| % lactam in solvent | Mixing method | Observations of solvent solution | Observations when added to M30 @ 5% |
|---|---|---|---|
| 3% | Magnetic stirring 1 hour | ~25% of lactam solubilised. Particles visible. | Clear solution with a large quantity of particles visible |
| 4.2% | Magnetic stirring. 24 hours | ~25% of lactam solubilised, Particles visible | Clear solution with a large quantity of particles visible |
| 4.2% | Magnetic stirring. 24 hours. Initially stirred for 2, 4 and 6 hours. No real changed observed during this time (all max. 25% solubilised). | ~25% of lactam solubilised, Particles visible. | Clear solution with a large quantity of particles visible |
| 4.2% | Magnetic stirring. 48 hours | ~25% of lactam solubilised, Particles visible. | Clear solution with a large quantity of particles visible |
| 2.1% | Magnetic stirring. 24 hours | ~50% of lactam solubilised, Particles visible. | Clear solution with a large quantity of particles visible |
| 2.1% | Magnetic stirring. 48 hours | ~75% of lactam solubilised, Particles visible. | Clear solution with a large quantity of particles visible |
| 4.2% | 20 minutes sonication. Temp reached 60-70 C. | 50% of lactam solubilised. Large number of particles visible. Very dark colour. | Clear solution with a large number of particles visible |
| 4.2% | 60 minutes sonication. Temp reached 110 C. | 75% of lactam solubilised. Very dark colour. | Some fragments visible in M30, suggesting partial breakdown of solvent. |
| 4.2% | 60 minutes sonication. Temp reached 80 C. | 75% of lactam solubilised. Very dark colour. | Fragments avoided due to temperature control. Clear solution with some small particles visible. |
| 2.1% | 20 minutes sonication. Temp reached 80 C. | 90% of lactam appeared to solubilise however small amount of 'burnt' spots visible. | Clear solution with a small number of black particles visible |
| 2.1% | 60 minutes sonication. Temp reached 110 C. | lactam solubilised. Very dark colour. | Some fragments visible in M30, suggesting partial breakdown of solvent. |
| 2.1% | Magnetic stirring, heated to 50 C. 8 hours. | ~50% of lactam solubilised, Particles visible. | Clear solution with a large quantity of particles visible |
| 3% | 20 minutes sonication. Temp reached 60-70 C. | ~75% of lactam solubilised. Particles visible | Clear solution with a large quantity of particles visible |
| 3% | 60 minutes sonication. Temp reached 80 C. | ~75% of lactam solubilised. Particles visible | Clear solution with a large quantity of particles visible |
| 1% | Magnetic stirring. 24 hours | ~75% of lactam solubilised, Particles visible. | Clear solution with a few particles visible |
| 1% | Magnetic stirring. 72 hours | ~90% of lactam solubilised, A few particles | Clear solution with a few particles visible |
| 1% | Magnetic stirring. 72 hours with temp. at 50 C. | ~99% of lactam solubilised, A tiny number of particles remained | Clear solution with a very small number of particles visible |
| 2.1% | 30 minutes sonication. Temp reached 90 C. | lactam appeared to solubilise however 'burnt' spots visible. | Clear solution with a small number of black particles visible |

Observation and Formulation Rules

Temperature and Colour Change

One of our first observations was the colour change which was visible in all successful (or partially successful) samples. We saw development of a slight amber tinge to the solution when some lactam was starting to become solubilised. This colour change progressed rapidly when samples exceeded 50 C, resulting in a dark brown colour. When the temperature reached 65 C, the dark brown colour was virtually opaque*.

*This level of temperature was only tested for the Polysorbate-20 and PEG-40 Hydrogenated Castor Oil variants.

From observations throughout the project, we concluded that ~50 C was the optimum temperature for solubilising the lactam.

Mixing Conditions

Very long periods of mechanical stirring (48-72 hours) resulted in improvements in solubilisation compared to shorter periods; however we did not find this length of mixing to be sufficient for full solubilisation. Ultrasonic mixing did prove to be far more successful and we concluded would be required for effective solubilisation, certainly with the shortlisted Polysorbate-20 and PEG-40 Hydrogenated Castor Oil candidates.

From all of the trials conducted, we believe with the right Ultrasonic mixing conditions (of energy versus batch size versus controlled max. 50 C temperature), efficient solubilisation could be achieved.

The invention claimed is:

1. An antimicrobial additive composition comprising a lactam and a hydrotrope, wherein (i) the lactam is of formula (I) or (II):

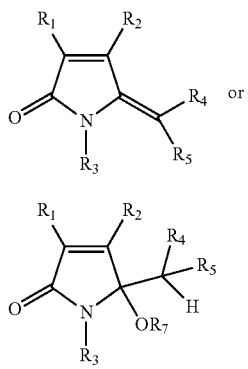

wherein:
R1 and R2 are each independently selected from the group consisting of hydrogen, halogen, alkyl, cycloalkyl, alkoxy, oxoalkyl, alkenyl, heterocyclyl, heteroaryl, aryl and arylalkyl;
R3 is selected from hydrogen, hydroxyl, alkyl, cycloalkyl, alkoxy, oxoalkyl, alkenyl, heterocyclyl, heteroaryl, cycloalkyl, aryl, arylalkyl and —C(O)CR6=CH2;
R4 and R5 are independently selected from hydrogen, aryl, heterocyclyl, heteroaryl, and arylalkyl;
R6 is selected from hydrogen and methyl; and
R7 is selected from hydrogen and —C(O)CR6=CH2; and
(ii) wherein the hydrotrope is selected from the group consisting of polyoxyethylene sorbitan fatty acid esters and polyoxyethylene derivatives of castor oil, and
(iii) wherein the hydrotrope is present at from 0.001 to 5% wt. of the composition.

2. The antimicrobial additive composition according to claim 1, wherein the additive composition is substantially free of further components.

3. The antimicrobial additive composition according to claim 1, wherein the lactam is selected from the group consisting of: 5-methylene-4-(4'-bromophenyl)-dihydropyrrol-2-one, 5-methylene-4-(2'-fluorophenyl)-dihydropyrrol-2-one, 5-methylene-4-phenyl-1H-pyrrol-2(5H)-one, methyl 2-(3-(4-fluorophenyl)-2-methylene-5-oxo-2,5-dihydro-1H-pyrrol-1-yl), 5-methylene-4-phenyl-dihydro-pyrrol-2-one, 3-Bromo-4-hexyl-5-(bromomethylene)-2(5H)-furanone, 4-(4-Trifluoromethyl)phenyl)-2(5H)-furanone, 5-Hydroxy-5-methyl-4-(2'-fluorophenyl)-dihydropyrrol-2-one, 5-(Thiophenyl-3-methylene)furan-(2H)-one, and mixtures thereof.

4. The antimicrobial additive composition according to claim 1, wherein the lactam is selected from the group consisting of: 5-methylene-4-(4'-bromophenyl)-dihydroprrol-2-one, 5-methylene-4-(2'-fluorophenyl)-dihydropyrrol-2-one, 5-methylene-4-phenyl-1H-pyrrol-2(5H)-one, methyl-2-(3-(4-fluorophenyl)-2-methylene-5-oxo-2,5-dihydro-1H-pyrrol-1-yl), and mixtures thereof.

5. The antimicrobial additive composition according to claim 1, wherein the lactam is present at from 0.001 to 50% wt. of the composition.

6. The antimicrobial additive composition according to claim 1, wherein the hydrotrope is a polyoxyethylene derivative of castor oil which comprises 40 oxyethylene units.

7. The antimicrobial additive composition according to claim 1, wherein the hydrotrope is a polyoxyethylene sorbitan fatty ester which comprises from 5 to 80 oxyethylene units.

8. The antimicrobial additive composition according to claim 1, which is a home or personal care composition.

9. The antimicrobial additive composition according to claim 8, wherein the home or personal care composition is selected from the group consisting of: a shampoo, a conditioner, a deodorant, a skin cleansing composition, and an antiperspirant.

10. The antimicrobial additive composition according to claim 8, wherein the home or personal care composition is selected from the group consisting of: a laundry composition, a hard surface cleaner and a toilet cleaner.

11. A method for making an antimicrobial additive composition comprising a lactam and a hydrotrope, comprising the steps: (a) directly mixing the lactam with the hydrotrope to form an antimicrobial additive composition; and (b) mixing the antimicrobial additive composition of step (a) with an aqueous carrier;
wherein
(i) the lactam is of formula (I) or (II):

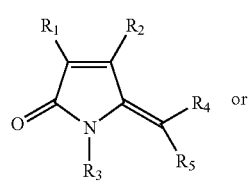

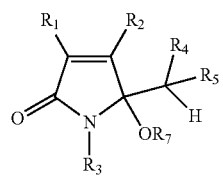

wherein:
R1 and R2 are each independently selected from the group consisting of hydrogen, halogen, alkyl, cycloalkyl, alkoxy, oxoalkyl, alkenyl, heterocyclyl, heteroaryl, aryl and arylalkyl;
R3 is selected from hydrogen, hydroxyl, alkyl, cycloalkyl, alkoxy, oxoalkyl, alkenyl, heterocyclyl, heteroaryl, cycloalkyl, aryl, arylalkyl and —C(O)CR6=CH2;
R4 and R5 are independently selected from hydrogen, aryl, heterocyclyl, heteroaryl, and arylalkyl;
R6 is selected from hydrogen and methyl; and
R7 is selected from hydrogen and —C(O)CR6=CH2; and
(ii) wherein the hydrotrope is selected from the group consisting of polyoxyethylene sorbitan fatty acid esters and polyoxyethylene derivatives of castor oil, and
(iii) wherein the hydrotrope is present at from 0.001 to 5% wt. of the composition.

12. A method of preventing or disrupting microbial growth comprising the step of applying an antimicrobial additive composition to the microbial growth, wherein the antimicrobial additive composition comprises a lactam and a hydrotrope, wherein (i) the lactam is of formula (I) or (II):

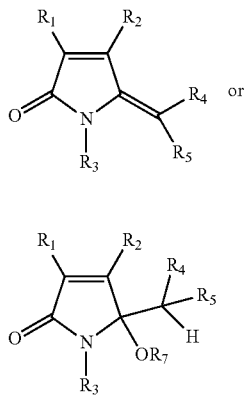

wherein:
R1 and R2 are each independently selected from the group consisting of hydrogen, halogen, alkyl, cycloalkyl, alkoxy, oxoalkyl, alkenyl, heterocyclyl, heteroaryl, aryl and arylalkyl;
R3 is selected from hydrogen, hydroxyl, alkyl, cycloalkyl, alkoxy, oxoalkyl, alkenyl, heterocyclyl, heteroaryl, cycloalkyl, aryl, arylalkyl and —C(O)CR6=CH2;
R4 and R5 are independently selected from hydrogen, aryl, heterocyclyl, heteroaryl, and arylalkyl;
R6 is selected from hydrogen and methyl; and
R7 is selected from hydrogen and —C(O)CR6=CH2; and (ii) wherein the hydrotrope is selected from the group consisting of polyoxyethylene sorbitan fatty acid esters and polyoxyethylene derivatives of castor oil, and (iii) wherein the hydrotrope is present at from 0.001 to 5% wt. of the composition.

* * * * *